US009528931B2

(12) United States Patent
Freese et al.

(10) Patent No.: US 9,528,931 B2
(45) Date of Patent: Dec. 27, 2016

(54) IMAGING SYSTEMS FOR OPTICAL COMPUTING DEVICES

(71) Applicant: Halliburton Energy Services, Inc., Houston, TX (US)

(72) Inventors: Robert Paul Freese, Pittsboro, NC (US); David Perkins, The Woodlands, TX (US); William Soltmann, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 203 days.

(21) Appl. No.: 14/409,080

(22) PCT Filed: Feb. 18, 2014

(86) PCT No.: PCT/US2014/016926
§ 371 (c)(1),
(2) Date: Dec. 18, 2014

(87) PCT Pub. No.: WO2015/126366
PCT Pub. Date: Aug. 27, 2015

(65) Prior Publication Data
US 2016/0266036 A1    Sep. 15, 2016

(51) Int. Cl.
*G01N 21/47* (2006.01)
*E21B 49/08* (2006.01)
*G01V 8/10* (2006.01)

(52) U.S. Cl.
CPC ............ *G01N 21/47* (2013.01); *E21B 49/081* (2013.01); *E21B 2049/085* (2013.01);
(Continued)

(58) Field of Classification Search
CPC .... G01V 8/10; E21B 49/081; E21B 2049/085; E21B 49/08; G01N 21/84
See application file for complete search history.

(56) References Cited

U.S. PATENT DOCUMENTS 5,918,960 A * 7/1999 Hopwood .............. G07D 7/121
                                              356/71
6,040,905 A   3/2000 Cheng et al.
(Continued)

FOREIGN PATENT DOCUMENTS

EP      1484600 A2    12/2004
WO   2015126366 A1    8/2015

OTHER PUBLICATIONS

International Search Report and Written Opinion for PCT/US2014/016926 dated Nov. 26, 2014.

*Primary Examiner* — Francis M Legasse, Jr.
(74) *Attorney, Agent, or Firm* — McDermott Will & Emery LLP; Tenley Krueger

(57) ABSTRACT

One disclosed optical computing device includes a sampling window arranged on a housing, an electromagnetic radiation source configured to emit electromagnetic radiation, the electromagnetic radiation being configured to optically interact with a substance outside of the sampling window, at least one integrated computational element (ICE) core arranged to optically interact with the electromagnetic radiation, and a detector arranged to receive the electromagnetic radiation following its optical interaction with the substance and the at least one ICE core and generate an output signal corresponding to a characteristic of the substance, wherein the electromagnetic radiation impinges upon the surfaces of the sampling window at an angle of incidence from normal to the sampling window, and wherein specular reflected light reflects off the sampling window at an opposing angle of incidence, the specular reflected light emanating away from the sampling window such that it is not detected by the detector.

21 Claims, 2 Drawing Sheets

(52) U.S. Cl.
CPC ........... *G01N 2021/4702* (2013.01); *G01N 2021/4704* (2013.01); *G01V 8/10* (2013.01)

(56) References Cited

U.S. PATENT DOCUMENTS

| | | |
|---|---|---|
| 6,687,002 B2 | 2/2004 | Stehle et al. |
| 6,917,723 B1 | 7/2005 | Tamburrini et al. |
| 2012/0033700 A1* | 2/2012 | Soejima ............... H01S 3/0627 372/50.1 |
| 2013/0140463 A1* | 6/2013 | Myrick ................. G01N 21/55 250/341.8 |
| 2013/0286398 A1 | 10/2013 | Freese et al. |

* cited by examiner

IMAGING SYSTEMS FOR OPTICAL COMPUTING DEVICES

BACKGROUND

The present disclosure generally relates to systems and methods of optical computing and, more specifically, to improved imaging systems for an optical train in optical computing devices.

Optical computing devices, also commonly referred to as "opticoanalytical devices," can be used to analyze and monitor a sample substance in real time. Such optical computing devices will often employ a light source that emits electromagnetic radiation that either reflects from or is transmitted through the sample and optically interacts with an optical processing element to determine quantitative and/or qualitative values of one or more physical or chemical properties of the substance being analyzed. The optical processing element may be, for example, an integrated computational element (ICE). One type of an ICE is an optical thin film interference device, also known as a multivariate optical element (MOE). Each ICE can be designed to operate over a continuum of wavelengths in the electromagnetic spectrum from the UV to mid-infrared (MIR) ranges, or any sub-set of that region. Electromagnetic radiation that optically interacts with the sample substance is changed and processed by the ICE so as to be measured by a detector. The output of the detector is then correlated to a physical or chemical property of the substance being monitored.

Some optical computing devices optically interact with the sample substance via a sampling window that separates the internal components of the optical computing device from the sample substance. The light that impinges upon the sample substance via the sampling window is dispersed by the substance and reflected back through the sampling window so that it can be collected and quantified by a detector associated with the optical computing device. The sensitivity and accuracy of some optical computing devices, however, can be limited by stray light that emanates primarily from the sampling window interface (both front and back surfaces). Such stray light can dilute, warp, or otherwise mask the light of interest that is reflected from the sample substance. As a result, light reflected off the sampling window and sensed by the detector can inaccurately detect the information of interest.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
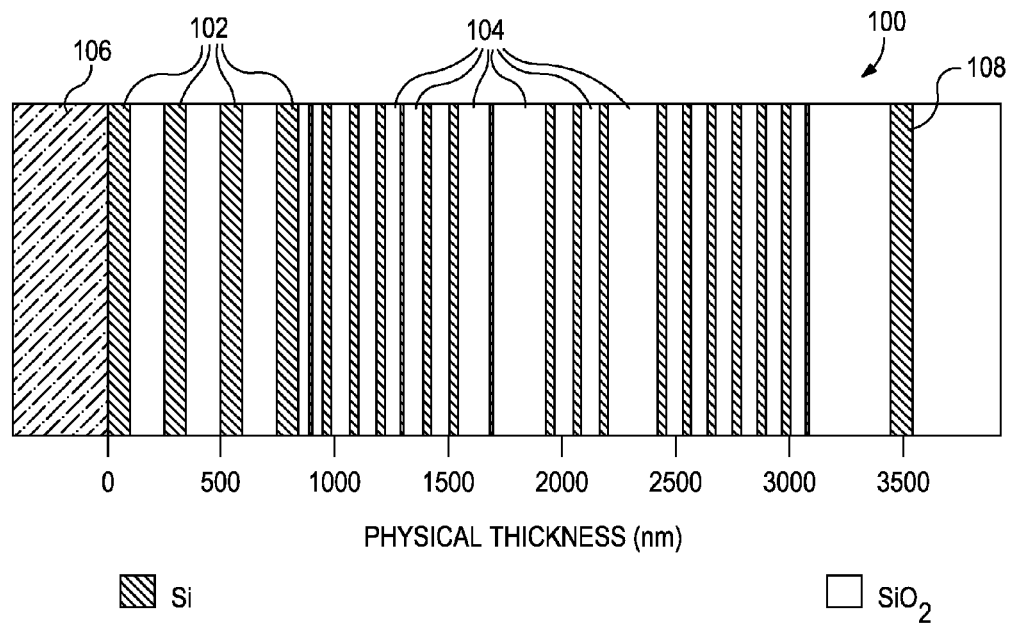
FIG. 1 illustrates a traditional integrated computation element, according to one or more embodiments.

The present disclosure generally relates to systems and methods of optical computing and, more specifically, to improved imaging systems for an optical train in optical computing devices.

The embodiments of the optical computing devices described herein include improved imaging systems that move the light source off-center and thereby enable greater discrimination between the light of interest that emanates from the sample substance and the unwanted stray light that is primarily generated through reflection off the sampling window. As described herein, the light from the optical computing device is able to uniformly illuminate the sample substance, which reflects the light back to a lens to be collected by a detector. Moving the light source off-center or otherwise at an angle with respect to the sampling window allows any stray light reflections generated by the sampling window to emanate at an angle directed away from the detector so as to not interfere with the reflected light of interest obtained from the sample substance. Consequently, the detector senses only the light coming from the sample substance, rather than a combination of light from the sample substance and the sampling window. Such embodiments may be able to dramatically increase the sensitivity and detectability limits of optical computing devices. Such enhanced sensitivity and detectability may enable the detection of key additives and ingredients in a sample substance, such as cement powders and drilling fluids.

The optical computing devices described herein may be used in the oil and gas industry, such as for monitoring and detecting components in subterranean treatment fluids that may be used in chosen downhole applications, such as drilling, cementing, fracturing, acidizing, production, formation fluids, etc. The optical computing devices described herein may specifically be employed advantageously to study and monitor components of such fluids, for example, certain additives that may be present in a drilling fluid or any of the other fluids listed above. The methods and apparatus described herein may be specifically advantageous for detecting trace components of such fluids. It will be appreciated, however, that the optical computing devices described herein may equally be used in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "substance," or variations thereof, refers to at least a portion of matter or material of interest to be tested or otherwise evaluated with the help of the optical computing devices described herein. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders (e.g., cements, concretes, etc.), drilling fluids (i.e., "muds"), glasses, mixtures, combinations thereof. Examples of such substances may include, but are not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, tracers, bridging agents, viscosifying agents, fracturing fluids, formation fluids, or any oilfield fluid, chemical, or substance commonly found in the oil and gas industry. The substance may also refer to solid materials such as, but not limited to, rock formations, concrete, solid wellbore surfaces, wellbore tools, pipes or flow lines, and solid surfaces of any wellbore tool or projectile (e.g., balls, darts, plugs, etc.).

As used herein, the term "characteristic" or "characteristic of interest" refers to a chemical, mechanical, or physical property of a substance or a sample of the substance. The characteristic of the substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (e.g., solid, liquid, gas, emulsion, mixtures thereof, etc.), and the like.

As used herein, the term "electromagnetic radiation" refers to radio waves, microwave radiation, terahertz, infrared and near-infrared radiation, visible light, fluorescent light, ultraviolet light, X-ray radiation and gamma ray radiation.

As used herein, the phrase "optically interact" or variations thereof refers to the reflection, transmission, scattering, diffraction, or absorption of electromagnetic radiation either on, through, or from an optical processing element (e.g., an integrated computational element) or a substance being analyzed with the optical computing device. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an integrated computational element (ICE). The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art.

Referring to FIG. 1, illustrated is an exemplary integrated computational element 100 that may be used in the optical computing devices described herein, according to one or more embodiments. In operation, the integrated computational element 100 (hereafter "ICE core 100") is capable of distinguishing electromagnetic radiation related to a characteristic of interest of a substance from electromagnetic radiation related to other components of the substance. As illustrated, the ICE core 100 includes a plurality of alternating thin film layers shown as layers 102 and 104. The first layers 102 are made of a material that exhibits a high index of refraction, such as silicon (Si), and the second layers 104 are made of a material that exhibits a low index of refraction, such as quartz ($SiO_2$). Other examples of materials that might be used include, but are not limited to, niobia and niobium, germanium and germania, MgF, SiO, and other high and low index materials generally known in the art. The layers 102, 104 are strategically deposited on an optical substrate 106, such as BK-7 optical glass. In other embodiments, the substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the substrate 106 in FIG. 1), the ICE core 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE core 100 depicted in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 will be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength are set to the regression weightings described with respect to a known equation, or data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE core 100 is configured to perform the dot product of the received electromagnetic radiation and the wavelength dependent transmission function of the ICE core 100. The wavelength dependent transmission function of the ICE core 100 is dependent on the substrate, the material refractive index of each layer, the number of layers 102, 104 and thickness of each layer 102, 104. As a result, the output light intensity of the ICE core 100 is related to the characteristic or analyte of interest.

As further explanation, accurately determining the regression vector of the characteristic of interest in the sample substance provides a means for an optical computing device to determine or otherwise calculate a concentration of said characteristic in the sample substance. The regression vector for each characteristic may be determined using standard procedures that will be familiar to one having ordinary skill in the art. For example, analyzing the spectrum of the sample substance may include determining a dot product of the regression vector for each characteristic of the sample substance being analyzed. As one of ordinary skill in art will recognize, a dot product of a vector is a scalar quantity (i.e., a real number). While the dot product value is believed to have no physical meaning by itself (e.g., it may return a positive or negative result of any magnitude), comparison of the dot product value of a sample substance with dot product values obtained for known reference standards and plotted in a calibration curve may allow the sample substance dot product value to be correlated with a concentration or value of a characteristic, thereby allowing unknown sample substances to be accurately analyzed.

To determine the dot product, one multiplies the regression coefficient of the regression vector at a given wavelength by the spectral intensity at the same wavelength. This process is repeated for all wavelengths analyzed, and the products are summed over the entire wavelength range to yield the dot product. Those skilled in the art will recognize that two or more characteristics may be determined from a single spectrum of the sample substance by applying a corresponding regression vector for each characteristic.

In practice, it is possible to derive information from electromagnetic radiation interacting with a sample substance by, for example, separating the electromagnetic radiation from several samples into wavelength bands and performing a multiple linear regression of the band intensity against a characteristic of interest determined by another measurement technique for each sample substance. The measured characteristic may be expressed and modeled by multiple linear regression techniques that will be familiar to one having ordinary skill in the art. Specifically, if y is the measured value of the concentration or characteristic, y may be expressed as in Equation 1:

$$y = a_0 + a_1 w_1 + a_2 w_2 + a_3 w_3 + a_4 w_4 + \ldots \qquad \text{Equation (1)}$$

where each 'a' is a constant determined by the regression analysis and each 'w' is the light intensity for each wavelength band. Depending on the circumstances, the estimate obtained from Equation (1) may be inaccurate, for example, due to the presence of other characteristics within the sample substance that may affect the intensity of the wavelength bands. A more accurate estimate may be obtained by expressing the electromagnetic radiation in terms of its principal components.

To obtain the principal components, spectroscopic data may be collected for a variety of similar sample substances using the same type of electromagnetic radiation. For example, following exposure to each sample substance, the electromagnetic radiation may be collected and the spectral intensity at each wavelength may be measured for each sample substance. This data may then be pooled and subjected to a linear-algebraic process known as singular value decomposition (SVD) in order to determine the principal components. Use of SVD in principal component analysis will be well understood by one having ordinary skill in the art. Briefly, however, principal component analysis is a dimension reduction technique that takes 'm' spectra with 'n' independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. Normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Equation (2):

$$x_1 z_1 + x_2 z_2 + \ldots + x_n z_n \qquad \text{Equation (2)}$$

The scalar multipliers $x_n$ may be considered the "magnitudes" of the principal components in a given electromagnetic radiation sample when the principal components are understood to have a standardized magnitude as provided by normalization.

Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Moreover, because the principal components are orthogonal to each other, the dot product of any principal component with any other principal component is zero. Physically, this means that the components do not spectrally interfere with each other. If data is altered to change the magnitude of one component in the original electromagnetic radiation signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude, whether positive or negative.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of the characteristic of the sample substance based upon the information carried by the electromagnetic radiation that has interacted with that sample substance. Differences observed in spectra of sample substances having varying quantities of an analyte or values of a characteristic may be described as differences in the magnitudes of the principal components. Thus, the concentration of the characteristic may be expressed by the principal components according to Equation (3) in the case where four principal components are used:

$$y=a_0+a_1x_1+a_2x_2+a_3x_3+a_4x_4 \qquad \text{Equation (3)}$$

where 'y' is a concentration or value of a characteristic, each a is a constant determined by the regression analysis, and $x_1$, $x_2$, $x_3$ and $x_4$ are the first, second, third, and fourth principal component magnitudes, respectively. Equation (3) may be referred to as a regression vector. The regression vector may be used to provide an estimate for the concentration or value of the characteristic for an unknown sample.

Regression vector calculations may be performed by a computer with appropriate software, based on spectrograph measurements of electromagnetic radiation by wavelength. The spectrograph system spreads the electromagnetic radiation into its spectrum and measures the spectral intensity at each wavelength over the wavelength range. Using Equation (3), the computer may read the intensity data and decompose the electromagnetic radiation sample into the principal component magnitudes $x_n$ by determining the dot product of the total signal with each component. The component magnitudes are then applied to the regression equation to determine a concentration or value of the characteristic.

To simplify the foregoing procedure, however, the regression vector may be converted to a form that is a function of wavelength so that only one dot product is determined. Each normalized principal component vector $z_n$ has a value over all or part of the total wavelength range. If each wavelength value of each component vector is multiplied by the regression constant and corresponding to the component vector, and if the resulting weighted principal components are summed by wavelength, the regression vector takes the form of Equation (4):

$$y=a_0+b_1u_1+b_2u_2+\ldots+b_nu_n \qquad \text{Equation (4)}$$

where $a_0$ is the first regression constant from Equation (3), $b_n$ is the sum of the multiple of each regression constant $a_n$ from Equation (3) and the value of its respective normalized regression vector at wavelength 'n', and $u_n$ is the intensity of the electromagnetic radiation at wavelength 'n'. Thus, the new constants define a vector in wavelength space that directly describes a concentration or characteristic of a sample substance. The regression vector in the form of Equation (4) represents the dot product of an electromagnetic radiation sample with this vector.

Normalization of the principal components provides the components with an arbitrary value for use during the regression analysis. Accordingly, it is very unlikely that the dot product value produced by the regression vector will be equal to the actual concentration or characteristic value of a sample substance being analyzed. The dot product result is, however, related (e.g., proportional or having a logarithmic or exponential relationship) to the concentration or characteristic value. As discussed above, the relationship may be determined by measuring one or more known calibration samples by conventional means and comparing the result to the dot product value of the regression vector. Thereafter, the dot product result can be compared to the value obtained from the calibration standards in order to determine the concentration or characteristic of an unknown sample being analyzed.

Figure 2:
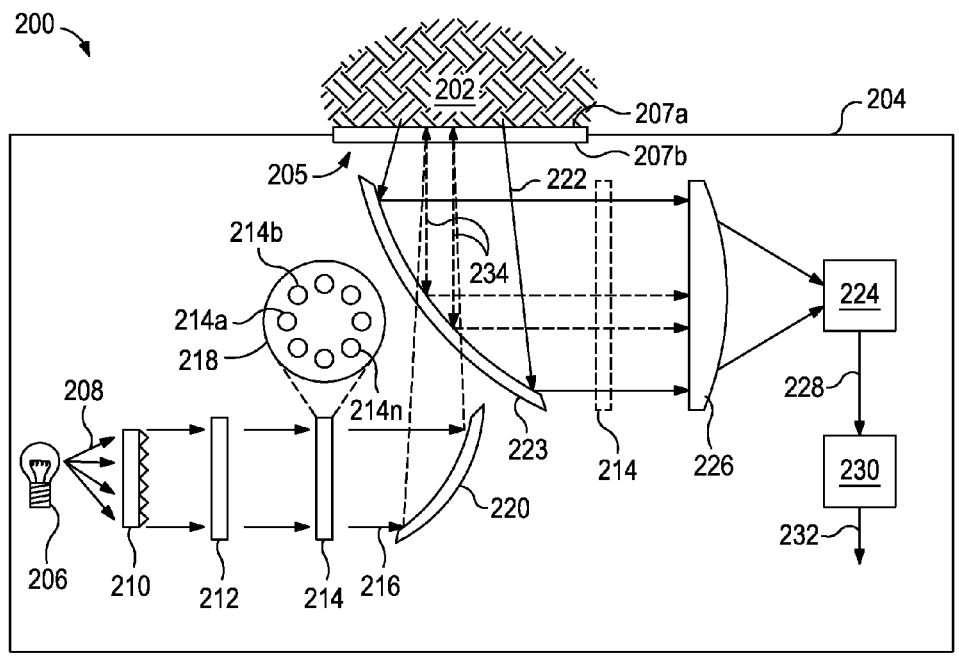
FIG. 2 illustrates an exemplary optical computing device for monitoring a substance, according to one or more embodiments.

Referring now to FIG. 2, illustrated is an exemplary optical computing device 200 that may be used for monitoring a substance 202, according to one or more embodiments. The optical computing device 200 (hereafter "the device 200") may be configured to determine a characteristic of interest in the substance 202 or a component or analyte present within the substance 202. As illustrated, the device 200 may include a housing 204 that generally encloses and otherwise encapsulates the internal components of the device 200. The interior walls of the housing 204 (and various other structural components of the housing 204) may be "blackened", or otherwise colored with dark colors, in order to be able to absorb any stray light.

A sampling window 205 may be included in or otherwise affixed to the housing 204. Note that the size and shape of sample window 205 may vary based on the particular application and use. The sampling window 205 may be configured to physically and optically separate the substance 202 from the internal components of the device 200. An outer surface 207a of the sampling window 205 may be in direct contact with the substance 202, while an inner surface 207b of the sampling window 205 may be exposed to the interior of the housing 204 and otherwise adjacent the internal components of the device 200. The sampling window 205 may be made from a variety of transparent, rigid or semi-rigid materials that are configured to allow transmission of light (i.e., electromagnetic radiation) therethrough. For example, the sampling window 205 may be made of, but is not limited to, glasses, plastics, semi-conductors, crystalline materials, polycrystalline materials, hot or cold-pressed powders, combinations thereof, or the like.

While being monitored by the optical computing device 200, the substance 202 may be either flowing or stagnant. For instance, in at least one embodiment, the substance 202 may be flowing within a defined flow path, such as a flow line, a pipeline, a wellbore, an annulus defined within a wellbore, or any flow lines or pipelines extending to/from a wellbore. In other embodiments, however, the substance 202 may be contained within a containment or storage vessel, such as mud pit (i.e., used for drilling fluids and the like).

As illustrated, the device 200 may include an electromagnetic radiation source 206 configured to emit or otherwise generate electromagnetic radiation 208. The electromagnetic radiation source 206 may be any device capable of emitting or generating electromagnetic radiation, as defined herein. For example, the electromagnetic radiation source 206 may be a light bulb, a light emitting diode (LED), a laser, any combination thereof, or the like. In other embodiments, the electromagnetic radiation source 206 may be used as an excitation source to produce emissive or fluorescent light from the substance 202. In such embodiments, X-ray, laser, LED, and ultraviolet sources (e.g., high pressure mercury of high pressure xenon) may be employed.

In some embodiments, a lens 210 may be configured to collect or otherwise receive the electromagnetic radiation 208 and direct a substantially uniform beam of light toward other components of the device 200 further down the optical train. The lens 210 may be any type of optical device configured to transmit or otherwise convey the electromagnetic radiation 208 as desired, such as a normal lens, a Fresnel lens, a diffractive optical element, a holographic graphical element, a mirror (e.g., a focusing mirror), or a type of collimator. In other embodiments, the lens 210 may be arranged at another location within the optical train or entirely omitted from the device 200, without departing from the scope of the disclosure.

The device 200 may further include an optical band pass filter 212 arranged to receive the electromagnetic radiation 208. The optical band pass filter 212 may operate by transmitting a certain wavelength band of the electromagnetic radiation 208 while blocking others. While shown following the lens 210 within the optical train of the device 200, it will be appreciated that the optical band pass filter 212 may be arranged at any point or location along the optical train, without departing from the scope of the disclosure. Moreover, in at least one embodiment, the optical band pass filter 212 may be omitted from the device 200, if desired.

The device 200 may further include at least one ICE core 214 arranged in the optical train and configured to optically interact with the electromagnetic radiation 208. The ICE core 214 may be similar to the ICE core 100 of FIG. 1, and therefore will not be described in detail. The ICE core 214 may be configured to receive the electromagnetic radiation 208 and transmit modified electromagnetic radiation 216 corresponding to a particular characteristic of the substance 202. In particular, the modified electromagnetic radiation 216 is electromagnetic radiation that has optically interacted with the ICE core 214, whereby an approximate mimicking of the regression vector corresponding to the characteristic of the substance 202 that the ICE core 214 is designed for is obtained.

While FIG. 2 depicts the ICE core 214 as receiving electromagnetic radiation 208 from the optical band pass filter 212, it will be appreciated that the ICE core 214 may be arranged at any point along the optical train of the device 200, without departing from the scope of the disclosure. For example, in one or more embodiments, the ICE core 214 (as shown in dashed) may be arranged within the optical train after the electromagnetic radiation 208 has optically interacted with the substance 202 via the sampling window 205 and equally obtain substantially the same results. In other embodiments, the ICE core 214 may generate the modified electromagnetic radiation 216 through reflection, instead of transmission therethrough.

Moreover, while only one ICE core 214 is shown in the device 200, embodiments are contemplated herein that include the use of at least two ICE cores that are configured to cooperatively determine the characteristic of interest in the substance 202. For example, two or more ICE cores may be arranged in series or parallel within the device 200 and configured to optically interact with the electromagnetic radiation 208 and thereby enhance sensitivities and detector limits of the device 200.

In yet other embodiments, it may be desirable to monitor more than one characteristic of the substance 202 at a time using the device 200. In such embodiments, individual and distinct ICE cores may be used to detect a corresponding particular and/or distinct characteristic of interest for the substance 202. As will be appreciated, various configurations for multiple ICE cores may be employed. For instance, in some embodiments, the characteristic can be analyzed sequentially using multiple ICE cores that are provided a single beam of electromagnetic radiation 208. In other embodiments, the multiple ICE cores may each receive individual beams of electromagnetic radiation 208 to optically interact therewith.

In yet other embodiments, as illustrated, multiple ICE cores (shown as ICE cores 214a, 214b, . . . , 214n) may be arranged on a movable assembly 218, such as a rotating disc. As depicted, the ICE cores 214a-n are arranged about or near the periphery of the rotating disc and circumferentially-spaced from each other. As the movable assembly 218 rotates, each ICE core 214a-n is able to be exposed to the electromagnetic radiation 208 for a short, distinct period of time. Advantages of this approach can include the ability to analyze multiple characteristics of the substance 202 using a single device 200 and the opportunity to assay additional characteristics by adding additional ICE cores 214a-n to the rotating disc. Upon optically interacting with the electromagnetic radiation 208, each ICE core 214a-n may be configured to produce individual beams of modified electromagnetic radiation 216, and each beam of modified electromagnetic radiation 216 may ultimately be time-multiplexed by a detector (e.g., the detector 224) in order to quantify each corresponding characteristic of interest. In one or more embodiments, at least one of the ICE cores 214a-n may be a neutral element configured to pass the electromagnetic radiation 208 unobstructed so that radiating deviations from the electromagnetic radiation source 206 can be detected and compensated for.

Alternatively, the movable assembly 218 may be characterized as a linear array (not shown) wherein the ICE cores 214a-n are laterally offset from each other. As the linear array oscillates, each ICE core 214a-n is able to be exposed to or otherwise optically interact with the electromagnetic radiation 208 for a distinct brief period of time. Those skilled in the art will appreciate that any of the foregoing configurations can further be used in combination with a series configuration in any of the present embodiments.

The modified electromagnetic radiation 216 generated by the ICE core 214 may be directed to an illumination mirror 220 configured to collect and re-direct the modified electromagnetic radiation 216 toward the sampling window 205 and the substance 202. In some embodiments, the illumination mirror 220 may have a focal point located adjacent the outer surface 207a of the sampling window 205 and otherwise within the substance 202. After passing through the sampling window 205, the modified electromagnetic radiation 216 impinges upon and optically interacts with the substance 202, including any components present within the substance 202. As a result, optically interacted radiation 222 is generated by and emanates from the substance 202. The optically interacted radiation 222 may be characterized as diffused light that is reflected off the substance 202.

The optically interacted radiation 222 may be collected by a collection mirror 223 arranged within the optical train of the device 200 and configured to convey the optically interacted radiation 222 to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

Prior to reaching the detector 224, the optically interacted radiation 222 may pass through a focusing lens 226 arranged within the optical train. The focusing lens 226 may be configured to receive and concentrate the optically interacted radiation 222 on the detector 224. Similar to the lens 210, the focusing lens 226 may be any type of optical device configured to transmit or otherwise convey the electromagnetic radiation 208 (e.g., the optically interacted radiation 222) as desired, such as a normal lens, a Fresnel lens, a diffractive optical element, a holographic graphical element, a mirror (e.g., a focusing mirror), or a type of collimator. In at least some embodiments, however, the focusing lens 226 may be omitted from the device 200, without departing from the scope of the disclosure.

The detector 224 may be configured to produce an output signal 228 in real-time or near real-time in the form of a voltage (or current) that corresponds to the particular characteristic of interest in the substance 202. The voltage returned by the detector 224 is a function of the concentration of the characteristic of interest of the substance 202. As such, the output signal 228 produced by the detector 224 and the concentration of the characteristic may be related, for example, directly proportional. In other embodiments, however, the relationship may correspond to a polynomial function, an exponential function, a logarithmic function, and/or a combination thereof.

The output signal 228 may be conveyed to or otherwise received by a signal processor 230 communicably coupled to the detector 224. The signal processor 230 may be a computer including a processor and a machine-readable storage medium having software instructions stored thereon, which, when executed by the processor 230, cause the device 200 to perform a number of operations, such as determining a characteristic of interest of the substance 202. For instance, the concentration of each characteristic detected with the device 200 can be fed into an algorithm operated by the signal processor 230. The algorithm can be part of an artificial neural network configured to use the concentration of each detected characteristic in order to evaluate the overall characteristic(s) or quality of the substance 202. In real-time or near real-time, the signal processor 230 may be configured to provide a resulting output signal 232 corresponding to a concentration of the characteristic of interest in the substance 202.

As illustrated in FIG. 2, and with the ICE core 214 positioned prior to the substance 202, the modified electromagnetic radiation 216 is directed toward the substance 202, and more particularly the sampling window 205, at an angle substantially normal to the sampling window 205. As a result, besides optically interacting with the substance 202 and producing the optically interacted radiation 222, the modified electromagnetic radiation 216 (i.e., the electromagnetic radiation 208) may also generate specular reflected light 234 that is derived from the sampling window 205. More particularly, the modified electromagnetic radiation 216 may be reflected off one or both the outer and inner surfaces 207a,b of the sampling window 205. Since the modified electromagnetic radiation 216 is directed normal to the sampling window 205, the specular reflected light 234 is reflected back toward the collection mirror 223 and simultaneously conveyed to the detector 224 along with the optically interacted radiation 222.

As will be appreciated in additional embodiments, with continued reference to FIG. 2, and with the ICE core 214 (shown in dashed) arranged in the optical train after the substance 202, the electromagnetic radiation 208 may be directed to and allowed to interact with the substance 202 via the sampling window 205. In these embodiments, the electromagnetic radiation 208 may generate the specular reflected light 234. More particularly, the electromagnetic radiation 208 may be reflected off one or both the outer and inner surfaces 207a,b of the sampling window 205. Since the electromagnetic radiation 208 is directed normal to the sampling window 205, the specular reflected light 234 is reflected back toward the collection mirror 223 and simultaneously conveyed to the ICE core 214 (shown in dashed) along with the optically interacted radiation 222.

As will be appreciated, the specular reflected light 234 is not related to the substance 202 or its spectral fingerprint, but instead encompasses modified electromagnetic radiation 216 (or electromagnetic radiation 208) that has reflected off the surfaces 207a,b of the sampling window 205. As a result, the signal exhibited by the specular reflected light 234 does not increase the detection capabilities of the device 200 but instead masks the optically interacted radiation 222 and negatively affects its detection capabilities. If not effectively reduced or otherwise prevented, the specular reflected light 234 may distort the optically interacted radiation 222 and result in substantially reduced accuracy, precision, sensitivity, and limits of detection for the device 200. For example, distortions include, but are not limited to, large bias voltages observed in the detector 224, lower resolution in spatial images, detector saturation effects, combinations thereof, or the like.

In some embodiments, reflection reducing techniques including anti-reflective (AR) coatings, such as a thin film interference structures, graded index coatings or, reflection-reducing microstructures, may be applied to the inner and/or outer surfaces 207a,b of the sampling window 205 with the intention of reducing the intensity of the specular reflected light 234. With many types of substances 202, however, AR coatings are often ineffective as applied to the outer surface 207a of the sampling window 205. For example, the substance 202 may chemically react with an AR coating thereby contaminating the substance 202 or compromising the effectiveness of the AR coating. In other cases, the substance 202 may abrade and/or erode the AR coating (especially over time), particularly if the substance 202 is moving and in contact with the outer surface 207a, and even more so if the substance 202 includes abrasive powders or components.

In some cases, the specular reflection reducing method (e.g., AR coating or microstructure) applied to either the inner or outer surfaces 207a,b of the sampling window 205 may also be insufficient to sufficiently reduce the contaminating signal to acceptable levels. For example, it has been determined that broadband AR coatings may only reduce the reflectance down to a window-to-sample ratio of about 10:1, thus limiting the sensitivity to analytes or characteristics whose concentrations exceeded 10% and all but eliminating the ability to detect additives to the substance 202. Thus, in many applications, common AR coating strategies known to those skilled in the art may either not be sufficient and/or available to reduce the detrimental signals of the specular reflected light 234 to acceptable levels.

To entirely eliminate or at least reduce the adverse effects of the specular reflected light 234, the structural configuration of the optical train of the device 200 (i.e., from the electromagnetic radiation source 206 to the detector 224) may be modified. In one embodiment, for example with the ICE core 214 (shown in dashed) arranged in the optical train after the substance 202, the angle at which the electromagnetic radiation 208 impinges upon the sampling window 205 may be moved off-center and otherwise to an angle offset from normal. As a result, the electromagnetic radiation 208 may impinge upon the sampling window 205 at an angle of incidence, and the specular reflected light 234 may consequently reflect off the sampling window 205 at an opposing angle of incidence. As a result, while the electromagnetic radiation 208 is able to optically interact with the substance 202 through the sampling window 205, only the diffused light derived from the substance 202 (e.g., the optical signal of interest) is collected and conveyed to the detector 224, while the specular reflected light 234 is directed away from the detector 224 at the opposing angle of incidence. As will be appreciated, this may enable far greater discrimination between the dispersed or diffused light emanating from the substance 202 and the unwanted stray light derived primarily from optical reflections off the inner and outer surfaces 207a,b of the sampling window 205.

Figure 3:
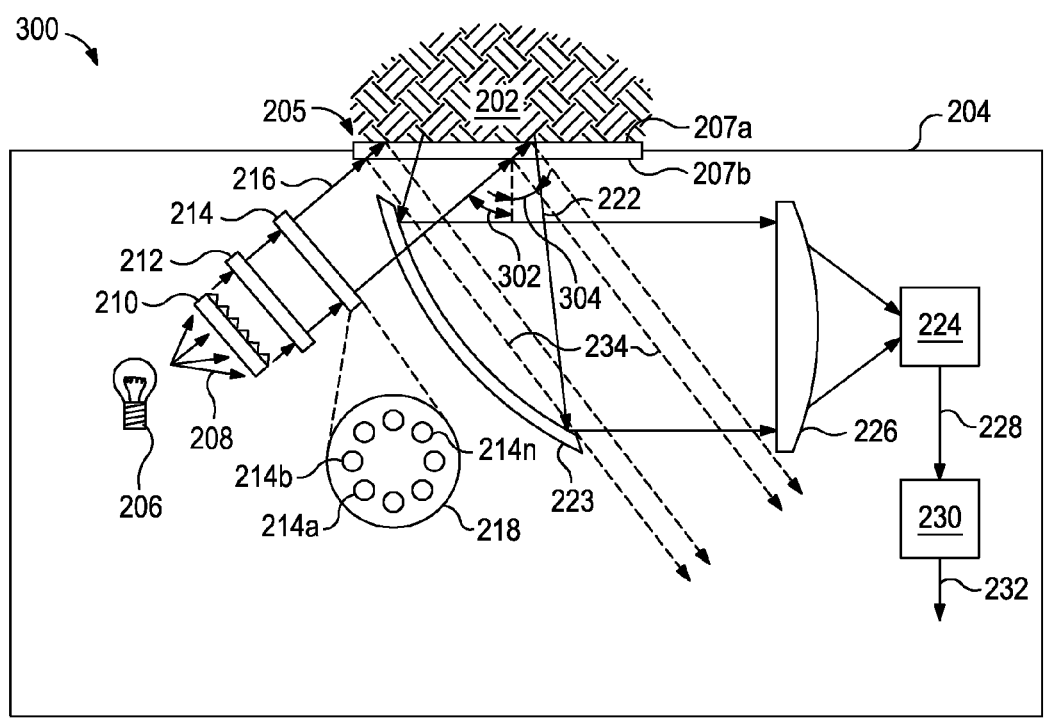
FIG. 3 illustrates another exemplary optical computing device for monitoring a substance, according to one or more embodiments.

Referring now to FIG. 3, with continued reference to FIG. 2, illustrated is another optical computing device 300 that may be used for monitoring the substance 202, according to one or more embodiments. The optical computing device 300 (hereafter "the device 300") may be similar in some respects to the device 200 of FIG. 2 and therefore may be best understood with reference thereto, where like numerals represent like components not described again in detail. As described below, the optical train of the device 300 (i.e., the internal components of the device 300 from the electromagnetic radiation source 206 to the detector 224) may be configured so as to eliminate or at least reduce the adverse effects of the specular reflected light 234, thereby increasing the sensitivity and detectability limits of the device 300.

As illustrated, the device 300 again includes the housing 204 and the sampling window 205 that separates the substance 202 from the internal components of the device 300 and otherwise allows the electromagnetic radiation 208 emitted from the electromagnetic radiation source 206 to optically interact with the substance 202. In some embodiments, the lens 210 may be included in the optical train of the device 300 to collect the electromagnetic radiation 208 and direct a substantially uniform beam of light toward other components of the device 300 within the optical train. In other embodiments, the lens 210 may be omitted from the device 300, without departing from the scope of the disclosure. The device 300 may also optionally include the optical band pass filter 212 in the optical train, as generally described above.

The device 300 may further include the ICE core 214 arranged in the optical train and configured to optically interact with the electromagnetic radiation 208 and transmit modified electromagnetic radiation 216 corresponding to a particular characteristic of the substance 202. Again, it will be appreciated that the ICE core 214 may be arranged at any point along the optical train of the device 300, without departing from the scope of the disclosure. For example, in one or more embodiments, the ICE core 214 may alternatively be arranged within the optical train after the sampling window 205 and otherwise after the electromagnetic radiation 208 has optically interacted with the substance 202 and equally obtain substantially the same results. For purposes of the present discussion in conjunction with the illustrated embodiment in FIG. 3, however, the ICE core 214 will be described as being arranged in the optical train prior to the sampling window 205, but should not be considered limiting to the present disclosure.

Moreover, while only one ICE core 214 is shown in the device 300, embodiments are contemplated herein that include the use of two or more ICE cores, as generally described above with reference to the device 200. In one embodiment, as illustrated, multiple ICE cores (shown as ICE cores 214a, 214b, . . . , 214n) may again be arranged on a movable assembly 218, such as a rotating disc, as generally described above with reference to FIG. 2. Alternatively, the movable assembly 218 may be characterized as a linear array (not shown) wherein the ICE cores 214a-n are laterally offset from each other and the linear array oscillates such that each ICE core 214a-n is able to be exposed to or otherwise optically interact with the electromagnetic radiation 208 for a distinct brief period of time.

The modified electromagnetic radiation 216 may be directed toward the sampling window 205 and the substance 202 such that it may optically interact with the substance 202, including any components present therein, as generally described above. The modified electromagnetic radiation 216 is diffused by the substance 202 and results in optically interacted radiation 222 that emanates from the substance 202 and is gathered by the collection mirror 223 to be conveyed to the detector 224 for quantification of the corresponding signal. In at least one embodiment, the optically interacted radiation 222 may pass through a focusing lens 226 configured to concentrate the optically interacted radiation 222 on the detector 224. In other embodiments, however, the focusing lens 226 may be omitted, without departing from the scope of the disclosure.

As generally described above, the detector 224 may produce the output signal 228 corresponding to the particular characteristic of interest in the substance 202. The output signal 228 may be conveyed to and received by the signal processor 230, which may be configured to provide a resulting output signal 232 corresponding to a concentration of the characteristic of interest.

In the illustrated embodiment, the modified electromagnetic radiation 216 may be conveyed toward the sampling window 205 at a predetermined angle of incidence 302. The angle of incidence 302 may be any angle that is at least 1° offset from normal to the sampling window 205 and at least 1° less than the critical angle of the sampling window 205. In theory, one could have the evanescent wave interact with the substance 202 at angles greater than the critical angle, but the resulting optically interacted radiation 222 would be very small and generally challenging to detect.

As will be appreciated, the modified electromagnetic radiation 216 may be directed toward the sampling window 205 at the angle of incidence 302 either directly from the electromagnetic radiation source 206, or otherwise via one or more lenses, focusing mirrors (e.g., the illumination mirror 220 of FIG. 2), or other optical elements, without departing from the scope of the disclosure. The modified electromagnetic radiation 216 is able to uniformly illuminate the substance 202, which disperses the modified electromagnetic radiation 216 (e.g., in the form of the optically interacted radiation 222) toward the collection mirror 223 (or any other internal component of the device 300). Once gathered by the collection mirror 223, the modified electromagnetic radiation 216 may then be directed to the detector 224 for quantification.

With the modified electromagnetic radiation 216 being directed toward the sampling window 205 at the angle of incidence 302, any specular reflected light 234 emanating from the sampling window 205 will occur at an opposing angle of incidence 304. In accordance with Snell's law, the angle of incidence 302 and the opposing angle of incidence 304 are equal but opposite. As illustrated, both the inner and outer surfaces 207a,b of the sampling window 205 may generate corresponding portions of the specular reflected light 234 reflected from the sampling window 205 at the opposing angle of incidence 304.

Advantageously, the internal components of the device 300 are arranged and otherwise configured such that the specular reflected light 234 is reflected from the sampling window 205 in a way that it is not detectable by the detector 224. In other words, the specular reflected light 234 fails to directly impinge upon the detector 224, or otherwise be directed to the detector 224 with the collection mirror 223 (or any other internal component of the device 300). Consequently, the detector 224 senses only the signal emanating from the substance 202, rather than from the substance 202 plus the stray signals (i.e., the specular reflected light 234) derived from sampling window 205.

In the illustrated embodiment, the angle of incidence 302 is depicted as approximately 45° offset from normal to the sampling window 205, thereby rendering the opposing angle of incidence 304 at approximately −45° from normal. Those skilled in the art, however, will readily appreciate that the internal components of the device 300 may be configured and otherwise optically arranged so as to allow the angle of incidence 302 to be any angle ranging between about 1° offset from normal to the sampling window 205 to about 1° less than the critical angle of the sampling window 205, without departing from the scope of the disclosure. As a result, the opposing angle of incidence 304 may also be any angle ranging between about −1° offset from normal to the sampling window 205 to about −1° less than the critical angle of the sampling window 205. Depending on the projected opposing angle of incidence 304, the internal components of the device 300 along the optical train may be arranged so that the specular reflected light 234 is not detectable by the detector 224.

In accordance with the foregoing embodiments, bench top tests have demonstrated window-to-sample ratios of approximately 500:1, and in some cases ratios up to 900:1, thus increasing the sensitivity and detectability limits of the device 300 by a factor of at least 50 times or greater. It has been observed that the foregoing embodiments resulted in window-to-sample ratios of 15:1 and greater. As will be appreciated by those skilled in the art, sensitivity improvement associated with this order of magnitude may prove advantageous in enabling the detection of key additives and ingredients in the substance 202.

In at least one embodiment, the device 300 may be particularly useful in monitoring powders (e.g., cement powders) or reflective slurries, such as drilling fluid and their constituent ingredients as the substance 202. For instance, the device 300 may enable the real-time measurement and analysis of the cement powder blending process. Moreover, the device 300 may also enable control and real-time corrective feedback for drilling muds and their additives. Because of the angle of incidence 302 for the electromagnetic radiation 208 and the resulting opposing angle of incidence 304 for the secular reflected light 234, the device 300 may be able to deliver greater sensitivity and accuracy over prior optical computing devices, as well as the ability to detect substantially lower concentrations that are generally associated with additives.

In other embodiments, the device 300 may further include a curved or rectangular container (not shown) that houses the substance 202 for detection. In such embodiments, the sampling window 205 may be curved or otherwise able to receive the electromagnetic radiation at 90° or more to the collection light axis. The resulting scattered radiation in the form of optically interacted radiation 222 may then emanate from the substance 202 at normal incidence. As will be appreciated, such an embodiment may prove useful when the electromagnetic radiation 208 or the electromagnetic radiation source 206 are configured for fluorescence studies.

As used herein, the term "optical train" used in reference to the optical computing devices 200 and 300 refers to the optical path that extends from the electromagnetic radiation source 206 to the detector 224.

Embodiments disclosed herein include:

A. An optical computing device that includes a sampling window arranged on a housing and having an inner surface exposed to an interior of the housing and an outer surface exposed to a substance to be monitored, an electromagnetic radiation source configured to emit electromagnetic radiation into an optical train defined within the housing, the electromagnetic radiation being configured to optically interact with the substance, at least one integrated computational element (ICE) core arranged in the optical train and configured to optically interact with the electromagnetic radiation, and a detector arranged within the optical train and configured to receive the electromagnetic radiation following optical interaction with both the substance and the at least one ICE core, the detector being further configured to generate an output signal corresponding to a characteristic of the substance, wherein the electromagnetic radiation impinges upon the surfaces of the sampling window wherein specular reflected light reflects off the sampling window at an opposing angle of incidence, the specular reflected light emanating away from the sampling window such that it is not detected by the detector.

B. A method that includes emitting electromagnetic radiation from an electromagnetic radiation source arranged within a housing of an optical computing device, the electromagnetic radiation being emitted into an optical train that extends from the electromagnetic radiation source to a detector, optically interacting the electromagnetic radiation with at least one integrated computational element (ICE) core arranged in the optical train, conveying the electromagnetic radiation toward a sampling window arranged on the housing, the sampling window having an inner surface exposed to an interior of the housing and an outer surface exposed to a substance to be monitored, impinging the sampling window with the electromagnetic radiation at an angle of incidence from normal to the sampling window, reflecting specular reflected light off the sampling window at an opposing angle of incidence, optically interacting the electromagnetic radiation with the substance, receiving the electromagnetic radiation with the detector following optical interaction with both the substance and the at least one ICE core, and generating an output signal corresponding to a characteristic of the substance with the detector, and directing the specular reflected light such that it is not detected by the detector.

Each of embodiments A and B may have one or more of the following additional elements in any combination: Element 1: wherein the sampling window is made of a material selected from the group consisting of glass, plastic, a semiconductor, a crystalline material, a polycrystalline material, a hot or cold-pressed powder, or any combination thereof. Element 2: wherein the electromagnetic radiation source is at least one of a light bulb, a light emitting diode, a laser, X-ray, an ultraviolet excitation source, and any combination thereof. Element 3: further comprising an illumination mirror arranged in the optical train and configured to convey the electromagnetic radiation toward the sampling window and the substance at the angle of incidence. Element 4: further comprising an collection mirror arranged in the optical train following the sampling window and configured to convey the electromagnetic radiation toward the detector after the electromagnetic radiation optically interacts with the substance. Element 5: wherein the at least one ICE core is arranged within the optical train prior to the sampling window. Element 6: wherein the at least one ICE core is arranged within the optical train after the sampling window. Element 7: wherein the at least one ICE core comprises multiple ICE cores arranged on a movable assembly configured to move such that each ICE core is exposed to the electromagnetic radiation for a distinct period of time. Element 8: wherein the movable assembly is a rotating disc. Element 9: wherein the angle of incidence is any angle between at least 1° offset from normal to the sampling window and at least 1° less than a critical angle of the sampling window. Element 10: wherein the substance is a material selected from the group consisting of particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders (e.g., cements and concretes), drilling fluids, glasses, aqueous fluids, non-aqueous fluids (e.g., organic compounds, hydrocarbons, oil, a refined component of oil, and petrochemical products), acids, surfactants, biocides, bleaches, corrosion inhibitors, foamers and foaming agents, breakers, scavengers, stabilizers, clarifiers, detergents, treatment fluids, fracturing fluids, formation fluids, rock formations, concrete, solid wellbore surfaces, pipes or flow lines, and solid surfaces of any wellbore tool or projectile. Element 11: wherein the output signal has a window-to-sample ratio of at least 15:1.

Element 12: wherein conveying the electromagnetic radiation toward the sampling window comprises receiving the electromagnetic radiation with an illumination mirror arranged in the optical train, and directing the electromagnetic radiation toward the sampling window with the illumination mirror. Element 13: further comprising conveying the electromagnetic radiation toward the detector with a collection mirror after the electromagnetic radiation optically interacts with the substance, the collection mirror being arranged in the optical train following the sampling window. Element 14: further comprising optically interacting the electromagnetic radiation with the at least one ICE core prior to the sampling window within the optical train. Element 15: further comprising optically interacting the electromagnetic radiation with the at least one ICE core after the sampling window within the optical train. Element 16: wherein the at least one ICE core comprises multiple ICE cores arranged on a movable assembly, the method further comprising moving the movable assembly such that each ICE core is exposed to the electromagnetic radiation for a distinct period of time. Element 17: wherein the angle of incidence is any angle between at least 1° offset from normal to the sampling window and at least 1° less than a critical angle of the sampling window. Element 18: wherein the substance is a cement powder, the method further comprising monitoring the cement powder during a cement powder blending process. Element 19: wherein the substance is a drilling fluid, the method further comprising monitoring the drilling fluid to determine a concentration of at least one additive included in the drilling fluid.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:
1. An optical computing device, comprising:
 a sampling window arranged on a housing and having an inner surface exposed to an interior of the housing and an outer surface exposed to a substance to be monitored;

an electromagnetic radiation source configured to emit electromagnetic radiation into an optical train defined within the housing, the electromagnetic radiation being configured to optically interact with the substance;

at least one integrated computational element (ICE) core arranged in the optical train and configured to optically interact with the electromagnetic radiation; and a detector arranged within the optical train and configured to receive the electromagnetic radiation following optical interaction with both the substance and the at least one ICE core, the detector being further configured to generate an output signal corresponding to a characteristic of the substance, wherein the electromagnetic radiation impinges upon the surfaces of the sampling window wherein specular reflected light reflects off the sampling window at an opposing angle of incidence, the specular reflected light emanating away from the sampling window such that it is not detected by the detector.

2. The optical computing device of claim 1, wherein the sampling window is made of a material selected from the group consisting of glass, plastic, a semi-conductor, a crystalline material, a polycrystalline material, a hot or cold-pressed powder, or any combination thereof.

3. The optical computing device of claim 1, wherein the electromagnetic radiation source is at least one of a light bulb, a light emitting diode, a laser, X-ray, an ultraviolet excitation source, and any combination thereof.

4. The optical computing device of claim 1, further comprising an illumination mirror arranged in the optical train and configured to convey the electromagnetic radiation toward the sampling window and the substance at the angle of incidence.

5. The optical computing device of claim 1, further comprising an collection mirror arranged in the optical train following the sampling window and configured to convey the electromagnetic radiation toward the detector after the electromagnetic radiation optically interacts with the substance.

6. The optical computing device of claim 1, wherein the at least one ICE core is arranged within the optical train prior to the sampling window.

7. The optical computing device of claim 1, wherein the at least one ICE core is arranged within the optical train after the sampling window.

8. The optical computing device of claim 1, wherein the at least one ICE core comprises multiple ICE cores arranged on a movable assembly configured to move such that each ICE core is exposed to the electromagnetic radiation for a distinct period of time.

9. The optical computing device of claim 8, wherein the movable assembly is a rotating disc.

10. The optical computing device of claim 1, wherein the angle of incidence is any angle between at least 1° offset from normal to the sampling window and at least 1° less than a critical angle of the sampling window.

11. The optical computing device of claim 1, wherein the substance is a material selected from the group consisting of a particulate solid, a liquid, air, nitrogen, carbon dioxide, argon, helium, methane, ethane, butane, hydrogen sulfide, a slurry, an emulsion, a powder, a cement, a concrete, a drilling fluid, glasses, water, brine, an organic compound, a hydrocarbon, oil, a refined component of oil, an acid, a surfactant, a biocide, a bleach, a corrosion inhibitor, a foamer, a foaming agent, a breaker, a scavenger, a stabilizer, a clarifier, a detergent, a tracer, a bridging agent, a viscosifying agent, a treatment fluid, a fracturing fluid, a formation fluid, a rock formation, a solid wellbore surface, a wellbore tool, a pipe or a flow line, and a solid surface of any wellbore tool or projectile.

12. The optical computing device of claim 1, wherein the output signal has a window-to-sample ratio of at least 15:1.

13. A method, comprising:
emitting electromagnetic radiation from an electromagnetic radiation source arranged within a housing of an optical computing device, the electromagnetic radiation being emitted into an optical train that extends from the electromagnetic radiation source to a detector;

optically interacting the electromagnetic radiation with at least one integrated computational element (ICE) core arranged in the optical train;

conveying the electromagnetic radiation toward a sampling window arranged on the housing, the sampling window having an inner surface exposed to an interior of the housing and an outer surface exposed to a substance to be monitored;

impinging the sampling window with the electromagnetic radiation at an angle of incidence from normal to the sampling window;

reflecting specular reflected light off the sampling window at an opposing angle of incidence;

optically interacting the electromagnetic radiation with the substance;

receiving the electromagnetic radiation with the detector following optical interaction with both the substance and the at least one ICE core, and generating an output signal corresponding to a characteristic of the substance with the detector; and directing the specular reflected light such that it is not detected by the detector.

14. The method of claim 13, wherein conveying the electromagnetic radiation toward the sampling window comprises:
receiving the electromagnetic radiation with an illumination mirror arranged in the optical train; and directing the electromagnetic radiation toward the sampling window with the illumination mirror.

15. The method of claim 13, further comprising conveying the electromagnetic radiation toward the detector with a collection mirror after the electromagnetic radiation optically interacts with the substance, the collection mirror being arranged in the optical train following the sampling window.

16. The method of claim 13, further comprising optically interacting the electromagnetic radiation with the at least one ICE core prior to the sampling window within the optical train.

17. The method of claim 13, further comprising optically interacting the electromagnetic radiation with the at least one ICE core after the sampling window within the optical train.

18. The method of claim 13, wherein the at least one ICE core comprises multiple ICE cores arranged on a movable assembly, the method further comprising moving the movable assembly such that each ICE core is exposed to the electromagnetic radiation for a distinct period of time.

19. The method of claim 13, wherein the angle of incidence is any angle between at least 1° offset from normal to the sampling window and at least 1° less than a critical angle of the sampling window.

20. The method of claim 13, wherein the substance is a cement powder, the method further comprising monitoring the cement powder during a cement powder blending process.

21. The method of claim 13, wherein the substance is a drilling fluid, the method further comprising monitoring the drilling fluid to determine a concentration of at least one additive included in the drilling fluid.

* * * * *